United States Patent [19]

(12) United States Patent
Loudon et al.

(10) Patent No.: US 8,198,083 B1
(45) Date of Patent: Jun. 12, 2012

(54) ORGANOTYPIC SLICES OF THE CENTRAL NERVOUS SYSTEM

(76) Inventors: William Gunter Loudon, San Clemente, CA (US); Shengwen Li, Irvine, CA (US); Brent A. Dethlefs, Laguna Niguel, CA (US)

( * ) Notice: Subject to any disclaimer, the term of this patent is extended or adjusted under 35 U.S.C. 154(b) by 195 days.

(21) Appl. No.: 12/263,347

(22) Filed: Oct. 31, 2008

Related U.S. Application Data

(60) Provisional application No. 61/001,466, filed on Oct. 31, 2007, provisional application No. 61/046,040, filed on Apr. 18, 2008, provisional application No. 61/046,044, filed on Apr. 18, 2008.

(51) Int. Cl.
*C12N 5/07* (2006.01)
(52) U.S. Cl. ......... 435/347; 435/1.1; 435/325; 435/373; 435/395; 435/397
(58) Field of Classification Search .................. None
See application file for complete search history.

(56) References Cited

U.S. PATENT DOCUMENTS

| | | |
|---|---|---|
| 5,303,225 A | 4/1994 | Satoh et al. |
| 6,574,174 B1 | 6/2003 | Amble et al. |
| 6,590,856 B2 | 7/2003 | Tsukagoshi et al. |
| 6,700,862 B2 | 3/2004 | Tsukuda et al. |
| 6,771,587 B2 | 8/2004 | Nishiuchi et al. |
| 6,773,781 B2 | 8/2004 | Ohsawa et al. |
| 6,861,117 B2 | 3/2005 | Rijpers et al. |
| 6,990,055 B1 | 1/2006 | Nakamura et al. |
| RE39,463 E | 1/2007 | Ohsawa et al. |
| 7,157,278 B2 | 1/2007 | Jin |
| 7,163,545 B2 | 1/2007 | Yaszemski et al. |
| 7,279,332 B2 | 10/2007 | Frisen et al. |
| 7,319,035 B2 | 1/2008 | Vacanti et al. |
| 7,326,572 B2 | 2/2008 | Fisk et al. |
| 7,376,058 B2 | 5/2008 | Narumi et al. |
| 2005/0208029 A1 | 9/2005 | Umezawa et al. |
| 2007/0231302 A1 | 10/2007 | Trapp et al. |
| 2007/0237751 A1 | 10/2007 | Sanberg et al. |
| 2007/0269412 A1 | 11/2007 | Kopyov |
| 2007/0274979 A1 | 11/2007 | Gruskin et al. |
| 2007/0280989 A1 | 12/2007 | Shahar et al. |
| 2008/0004713 A1 | 1/2008 | Nakamura et al. |
| 2008/0020407 A1 | 1/2008 | Jamieson et al. |
| 2008/0025957 A1 | 1/2008 | Lapidot et al. |
| 2008/0025963 A1 | 1/2008 | Gruskin et al. |
| 2008/0031858 A1 | 2/2008 | Chan et al. |
| 2008/0031859 A1 | 2/2008 | Okano et al. |
| 2008/0031870 A1 | 2/2008 | Holmberg et al. |
| 2008/0038770 A1 | 2/2008 | Hansford et al. |
| 2008/0039389 A1 | 2/2008 | Weiss et al. |
| 2008/0044900 A1 | 2/2008 | Mooney et al. |
| 2008/0050812 A1 | 2/2008 | Cox et al. |

FOREIGN PATENT DOCUMENTS

| | | |
|---|---|---|
| WO | 9632467 A1 | 10/1996 |
| WO | 2006039582 A2 | 4/2006 |
| WO | 2006047299 A2 | 5/2006 |
| WO | 2006051405 A2 | 5/2006 |
| WO | 2006136953 A2 | 12/2006 |
| WO | 2007118242 A2 | 10/2007 |
| WO | 2007147165 A2 | 12/2007 |

OTHER PUBLICATIONS

Bratincsák et al. Ideggyogy Sz Mar. 30, 2007;60:124-9.*
Elias et al. J Vis Exp Jul. 11, 2007;6:235.*
Gogolla et al. Nat Protocol 2006;1:1165-71.*
Peyton. OpenWetWare 2004.*
Li et al.; A Biological Global Positioning System: Considerations for Tracking Stem Cell Behaviors in the Whole Body; Stem Cell Rev and Rep; 2010; 6:317-333.
Eitan et al.; Acellular Cardiac Extracellular Matrix as a Scaffold for Tissue Engineering: In Vitro Cell Support, Remodeling, and Biocompatibility; Tissue engineering: Part C; vol. 16; No. 4; 2010.
Engler et al.; Embroynic cardiomyocytes beat best on a matrix with heart-like elasticity: scar-like rigidity inhibits beating; Journal of Cell Science; 121; 3794-3802; 2008.
Engler et al.; Myotubes differentiate optimally on substrates with tissue-like stiffness: pathological implications for soft or stiff microenvironments; The Journal of Cell Biology; vol. 166; No. 6; 877-887; 2004.
Even-Ram et al.; Matrix Control of Stem Cell Fate; Cell 126: 645-647; 2006.
Li et al.; Stem Cell Therapy for Paediatric Malignant Brain Tumors: The Silver Bullet?; Oncology News 3; 10-14; 2008.
Li et al.; A novel and generalizable organotypic slice platform to evaluate stem cell potential for targeting pediatric brain tumors; Cancer Cell International 8; 2008.
Li et al.; Therapeutic Window, a Critical Developmental State for Stem Cell Therapies; Current Stem Cell Research & Therapy 5; 287-293; 2010.
Li et al.; Stem cell engineering for treatment of heart diseases: Potentials and challenges; Cell Biology International 33;255-267; 2009.
Müller et al.; Gene therapy: can neural stem cells deliver?; Nature Reviews—Neuroscience; vol. 7; pp. 75-84; Nature Publishing Group; Jan. 2006.
Dirks, Peter, Research Interests; www.sickkids.ca/Research/Dirks-Lab/Research-interests/index.html; internet page published on Dec. 9, 2004.
Kondo, Tom et al.; Persistence of a small subpopulation of cancer stem-like cells in the C6 glioma cell line; Proceeding of the National Academy of Sciences of the United Sates of America (PNAS); vol. 101; No. 3; 781-786; Jan. 20, 2004.
DiMuzio MD, Paul et al.; Tissue Engineering Applications to Vascular Bypass Graft Development: The Use of Adipose-Derived Stem Cells; NIH Public Access; J Vasc Surg. Author Manuscript; 45(Suppl A); 99-103; Jun. 2007.

(Continued)

*Primary Examiner* — Q. Janice Li

(57) ABSTRACT

An organotypic slice and a method of preparing an organotypic slice from a central nervous system tissue, wherein the organotypic slice comprises a brain slice obtained from a brain wherein mature synapses have not been established and the organotypic slice is seeded with a population of stem cells; wherein the organotypic slice has enhanced viability as compared to an organotypic slice comprising a similar brain slice not seeded with a population of stem cells.

10 Claims, 1 Drawing Sheet

OTHER PUBLICATIONS

Polleux, Franck et al.; The Slice Overlay Assay: A Versatile Tool to Study the Influence of Extracellular Signals on Neuronal Development, Science Signaling; Sci. STKE 2002; 136, p. 19, Jun. 11, 2002.

Yin, E. et al.; Gene expression changes in mouse brain after exposure to low-dose ionizing radiation; Int. J. Radial. Biol; Oct. 2003; vol. 79, No. 10; 759-775.

Koyama, Yutaka et al.; Production of monocyte chemoattractant protein-I and cytokine-induced neutrophil chemoattractant-I in rat brain is stimulated by intracerebroventricular administration of an endothelin ET B receptor agonist; Glial Cells; NeuroReport; vol. 18; No. 12; 1275-1279; Aug. 6, 2007.

Burke et al.; Modulation of Epileptiform Activity by Metabotropic Glutamate Receptors in Immature Rat Neocortex; Journal of Neurophysiology; vol. 73; No. 1; Jan. 1995.

Weiss, David S. et al.; Specific Patterns of Intrinsic Connections between Representation Zones in the Rat Motor Cortex; Cerebral Cortex; 4:205-214; Mar./Apr. 1994.

DiMuzio MD, Paul.; Tissue Engineering applications to vascular bypass graft development: The use of adipose-derived stem cells; Journal of Vascular Surgery; Jun. Supplement 2007; 99A-103A.

* cited by examiner

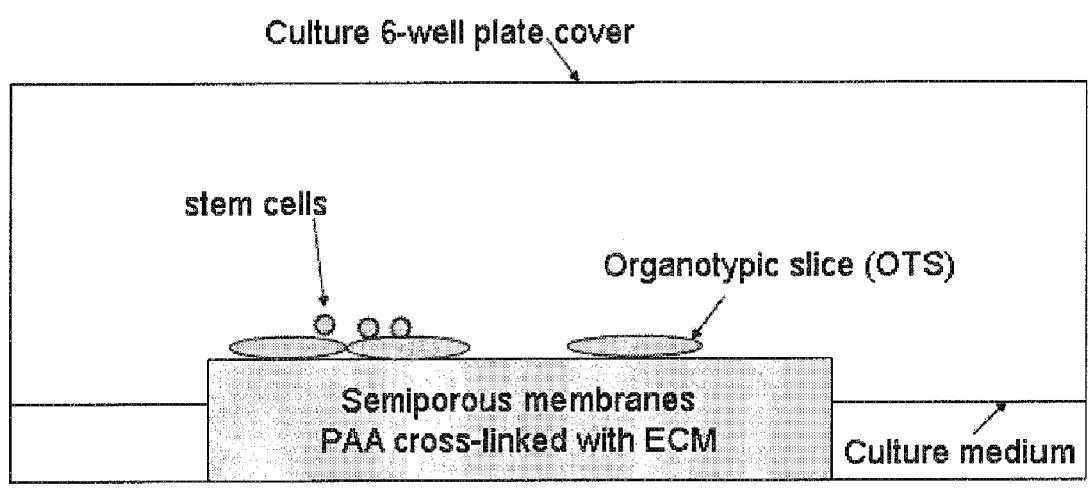

ORGANOTYPIC SLICES OF THE CENTRAL NERVOUS SYSTEM

CROSS REFERENCE

This application claims priority to U.S. provisional application Ser. No. 61/001,466 filed Oct. 31, 2007; U.S. provisional application Ser. No. 61/046,040 filed Apr. 18, 2008; and U.S. provisional application Ser. No. 61/046,044 filed Apr. 18, 2008; the specifications of which are incorporated herein by reference in its entirety.

FIELD OF THE INVENTION

The present invention is directed to a tissue slice derived from a central nervous system tissue of an animal. More particularly, the present invention is directed to a central nervous system tissue slice seeded with a population of stem cells.

BACKGROUND OF THE INVENTION

A major advance in the field of tissue culture and biological models has been the introduction of organotypic slice cultures. Organotypic slices are thin (micrometers) slices of an animal organ, which are cultured under conditions in which the slice retains the cellular composition, morphology, extracellular organization, and the physiological properties of the source organ, which presents a major advantage over using traditional in vitro cell culture methods. Organotypic slices have the advantage of being easier to use and manipulate than in vivo models such as rodents and primates. Moreover, organotypic cultures allow for the assessment of cellular, molecular, phenotypic, biochemical, and development characteristics, which enables, for example, the identification of factors that control neuronal adhesion, acquisition of cell-specific phenotypes, regulation of axonal and dendritic patterning, and development of tumor diseases. Organotypic slices may also be used to study cell migration, cell differentiation, cell-induced tissue injury repair, or even cell susceptibility to drugs.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1 is a side view of an organotypic slice, wherein the slice is placed atop a membrane inside a culture dish.

DESCRIPTION OF PREFERRED EMBODIMENTS

Other methods for preparing organotypic slices have been previously described. The disclosure of the articles Stoppini et al., 1991; Gahwiler et al., 1981; Raineteau et al., 2004; Ullrich et al., 2001; Whicks et al., 1968; Wildenthal et al., 1971; Corradino et al., 1973; Gangatirkar et al., 2007; Michalopolous et al., 2001; Michalopolous et al., 2004; and Eyupoglu et al., 2003 are incorporated in their entirety herein by reference.

The present invention features a novel organotypic slice and a method of preparing an organotypic slice. The organotypic slice is constructed from a central nervous system tissue. Organotypic slices of the present invention have clinical relevance as they can be used for a variety of experiments and/or procedures.

It was surprisingly found that co-culturing of an organotypic slice (e.g., derived from a central nervous system tissue) with a population of stem cells can help to maintain the viability (e.g., lifespan, shelf life) and/or integrity of the organotypic slice longer than if the organotypic slice was cultured without stem cells. Without wishing to limit the present invention to any theory or mechanism, it is believed that the lifespan of the organotypic slice can be extended by adding an amount of stem cells, and there may be a correlation between the number of stem cells and the lifespan of the slice. For example, the more stem cells, the longer the lifespan of the organotypic slice.

As used herein; the term "about" refers to plus or minus 10% of the referenced number. For example, an embodiment wherein an organotypic slice is about 300 µm thick includes an organotypic slice that is between 270 and 330 µm thick.

For any embodiment of the present invention, the term "genetically engineered mammal" includes a transgenic mammal, a mutant mammal, a null mammal, a gain-of-function mammal, a loss-of-function mammal, a knock-in mammal, or a knockout mammal. For example, in an embodiment wherein the population of stem cells is derived from a genetically engineered mouse, the population of stem cells may be derived from a transgenic mouse. For any embodiment of the present invention, the term "genetically engineered cell" includes a mutant cell, a knockout cell, a knock-in cell, a transgenic cell, or a cell having additional DNA (e.g, a plasmid).

For any embodiment of the present invention, the term "modified component" refers to a component that is reduced, decreased, depleted, ablated, increased, elevated, or mutated. For example, an embodiment of an organotypic slice having a modified astrocyte cellular component may be an organotypic slice having ablated astrocytes.

Preparation of Organotypic Slice

The method of the present invention comprises obtaining a brain from a mammal (e.g. a rodent). A mammal may include, for example, a human, a mouse, a rat, a rabbit, a dog, a primate, a guinea pig, a cat, a hamster, a pig, a chicken, a goat, a horse, or a cow.

Without wishing to limit the invention to any theory or mechanism, in some cases it may be advantageous if the organotypic slice is prepared from a genetically engineered mammal. For example, if the organotypic slice is prepared from the brain tissue of a genetically engineered mouse harboring a gene for green fluorescent protein (GFP) linked to a glial cell marker, it would likely be easier to monitor the location, the growth, the development, or the death of the glial cells because the GFP gene would enable the cell to be observed under a fluorescent microscope. Or, if a user wishes to overexpress a gene in the organotypic slice, the organotypic slice may be prepared from the tissue of a genetically engineered mammal that overexpresses that particular gene. Thus, in some embodiments, the organotypic slice is prepared from a genetically engineered mammal, for example, a genetically engineered mouse, a genetically engineered rat, a genetically engineered rabbit, a genetically engineered dog, a genetically engineered primate, a genetically engineered guinea pig, a genetically engineered cat, a genetically engineered hamster, a genetically engineered pig, a genetically engineered chicken, a genetically engineered goat, a genetically engineered horse, or a genetically engineered cow.

The present invention features an organotypic slice comprising a brain slice obtained from a brain wherein mature synapses have not been established.

The organotypic slice has enhanced viability as compared to an organotypic slice comprising a similar brain slice not seeded with a population of stem cells. In some embodiments, enhanced viability is determined by physical characteristics, such characteristics are well known to one of ordinary skill in the art.

In some embodiments, the enhanced viability allows the organotypic slice to live for more than about 6 months.

In some embodiments, the enhanced viability allows the organotypic slice to live for more than about 12 months.

In some embodiments, rodents (e.g., mice, or rats) at postnatal days 3-9 may be used for preparing organotypic slices (e.g., the brain is obtained from a rodent of an age between three to nine days). Previous studies have shown that brain tissues from rodents at postnatal days 3-9 show a high degree of plasticity and resistance to mechanical trauma resulting from slice preparation. At this age, basic synaptic connections have been established, particularly in the CA1 area of the hippocampus, but mature synapses have not yet been established in the brain, which normally develop during the following 2-3 weeks in vivo (De Simoni et al., 203, J. Physiol., 550, 135-147; Pokony et al., 1981, Brain Res. Bull., 7: 121-130). However, organotypic slices may be made from rodents older than 9 days. For example, organotypic slices prepared from brains of mature transgenic rodents can have specific utilities in the investigation of interaction between transplanted stem cells and residential cells in the OTS.

A variety of materials and solutions are needed for preparing organotypic slices. Materials can include but are not limited to cell culture inserts for six-well plates (Millicell® Sterilized culture plate insert, Millipore), six-well culture plates (Becton Dickinson); syringe 0.2 μm filter units (Nalgene); and filter paper (Millipore). Solutions can include but are not limited to Complete Hank's Balanced Salt Solution (Complete HBSS), low melting point (LMP) agarose, and slice culture medium (SCM). See Example 1 for recipes of solutions. Equipment includes but is not limited to an autoclave; a 37 degree C. water bath, binocular loop with back illumination, a centrifuge; an Incubator (5% CO2, humidified), an inverted microscope with long-distance working objectives (10×, 20×) with numerical aperture of about 0.6, a microwave oven; a Vibratome EMS OTS 4000 (Electron Microscopy Sciences), and an ultraviolet light for sterilization.

To isolate a brain from a postnatal rodent (e.g., rat), the rodent can be euthanized with an overdose of pentobarbital by intraperitoneal injection. In some embodiments, to isolate an embryonic brain, a pregnant female rodent is euthanized with carbon dioxide for about 5 minutes. The uterus is removed and placed in about 15 ml of Complete HBSS in a petri dish on ice.

Next, the brain is quickly removed from the skull and placed in a dish containing ice-cold Complete HBSS on ice. LMP agarose is poured into an individual plastic tissue embedding mold on ice. The temperature can be monitored using a thermometer. When the temperature approaches 38 degrees Celsius, as much Complete HBSS as possible is blotted from around the brain with a clean tissue (e.g., Kimwipe®). Then the brain is embedded in the LMP agarose and left to mold on ice for about 5 minutes. The agarose should harden.

The method of the present invention comprises preparing a brain slice. The embedded brains can be placed in a vibratome containing cold HBSS in the slicing chamber to which carbon dioxide and oxygen bubbles flow to maintain pH and metabolism. Coronal sections are sliced at 250 μm (for embryonic brains) or 300 μm (for postnatal brains) with the vibratome.

The brain slice is derived from a central nervous system tissue (e.g., a brain, a spinal cord). In some embodiments, the brain slice comprises one or more brain structures. For example, in some embodiments, a structure of the brain comprises a brainstem structure, a nigrostriatal structure, a hippocampal structure, a cortical structure, a cerebral cortex structure, a corpora striata structure, a rhinencephalon structure, a diencephalon structure, a thalamus structure, a hypothalamus structure, a pituitary structure, a pineal gland structure, a midbrain structure, a mesencephalon structure, a corpora quadrigemia structure, tegmentum structure, a hindbrain structure, a metencephalon structure, a cerebellum structure, a pons structure, a myelencephalon structure, a medulla oblongata structure, a spinal cord structure, a medulla structure, an amygdale structure, a substantia nigra structure, a caudate nucleus structure, a putamen structure, an olfactory structure, a septal region structure, a cingulated cortex structure, a tectum structure, an interior colliculi structure, a superior colliculi structure, or a combination thereof.

Without wishing to limit the present invention to any theory or mechanism, in some embodiments, the organotypic slice comprises any two or more brain structures that are anatomically connected in the native brain, for example, a cerebral cortex frontal lobe structure and a cerebral cortex parietal lobe structure; or a pons structure and a cerebellum structure. Using an organotypic slice comprising any two or more brain structures that are anatomically connected in the native brain may be advantageous because it may provide for a more physiologically accurate environment. For example, it is possible that the presence of a cellular component, such a neuron or glial cell, or a growth factor from one particular anatomic region of the brain is necessary for the execution of certain biological reactions in another anatomic region of the brain.

In some embodiments, the organotypic slice comprises any two or more brain structures that are not anatomically connected in the native brain, for example, an amygdala structure and an optic nerve structure or a pineal body structure and a hypothalamus structure. Using an organotypic slice comprising any two or more brain structures that are not anatomically connected in the native brain may be advantageous because it may provide for a more physiologically accurate environment. It is possible that the presence of a cellular component, such a neuron or glial cell, or a growth factor from one particular anatomic region of the brain is necessary for the execution of certain biological reactions in another anatomic region of the brain.

In some embodiments, the central nervous system tissue is cut at a boundary such that an endogenous tract of the central nervous system tissue is intact. In some embodiments, the central nervous system tissue is cut such that an endogenous tract of the central nervous system is intact and the central nervous system tissue comprises nuclei and/or a plurality of neurons and/or a functional region of the brain. For example, in some embodiments, the central nervous system tissue comprises an endogenous tract of the central nervous system and a plurality of substantia nigra neurons.

In some embodiments, the endogenous tract is derived from a subependymal zone, a hippocampus, a hippocampal commisures, an anterior commisure, an interthalamic commisures, a formix, a fimbriae, a corticospinal (pyramidal) tract, a corpus callosum, a cortico-hypothalamic tract, an olfactory tract, a pallido-cortical tract, a nigro-cortical tract, a motor tract, a medulla spinalis, a geniculate fibers, an anterior cerebrospinal fasciculus (direct pyramidal tract), a rubrospinal fasciculus, a dorsal and ventral spinocerebellar fascicule, a spinocerebellar tract, a dorsal (posterior) spinocerebellar tract, a ventral (anterior) spinocerebellar tract, a rostral spinocerebellar tract, a spinocuneocerebellar tract, a posterior funiculi, a vestibulospinal fasciculus, a pontospinal fasciculus, a spinothalamic fasciculus, a tectospinal fasciculus, a fasciculus gracilis, a fasciculus cuneatus, a ventral longitudinal bundle, a lateral lemniscus, a cortico mammillary tract, an amygdalofugal tract, a tectobulbar tract, an olfactory tracts, a cortico-mesencephalic tract, an optic tract, an optic radiations, a dorsal column-medial lemniscus system, an uncinate fasciculus, an occipitofrontal fasciculus, an optic radiation, a Meyer's loop of the optic radiation, or a combination thereof.

In some embodiments, a nucleus and/or functional region of the brain may include thalamus, hypothalamus (e.g, suprachiasmatic nucleus), pituitary, epithalamus, pineal body, red nucleus, subthalamus, substantia nigra, brain stem (e.g., dorsal raphe, locus coeruleus), spinal cord, pons, cerebellum (e.g., basal cerebellar nuclei, cerebellar cortex, lobules, folia), tectum, superior colliculus, inferior colliculus, periaquaductal nuclei, posterior commissure, superior olive, inferior olive, cerebral cortex, basal ganglia, corpus striatum, olfactory cortex, septum, anterior commissure, formix, subformical organ, corpus callosum, basal forebrain, olfactory tubercle, olfactory cortex, hippocampus, caudate nucleus, putamen, globus pallidus, ventral striatum, claustrum, amygdalar complex, nucleus accumbens septi, or a combination thereof.

As they are being cut, the slices are transferred using a large-opening flamed glass Pasteur pipette to a new dish containing ice-cold Complete HBSS. Other methods well known to one of ordinary skill in the art may be used to transfer the slices to new dishes. Without wishing to limit the present invention to any theory or mechanism, it is believed that using a large-opening glass Pasteur pipette is advantageous because it does not damage the tissue and reduces contamination.

In some embodiments, the tissue slices can be microdissected using a microdissecting knife and fine forceps.

Next, the tissue slices or microdissected tissue slices are carefully transferred to coated membranes of the culture inserts. A fine spatula can be used to transfer the slices and surrounding agarose to the membranes. Excess Complete HBSS is removed with a pipette such that an interface between the slice and the culture membrane exists. The slices are placed in a 37 degree C. incubator.

The method of the present invention further comprises seeding the organotypic slice with a population of stem cells. The population of stem cells can be inoculated into the organotypic slices after about 3 to 5 days post slice preparation. In some embodiments, a 2 µl suspension of a desired number of stem cells is inoculated via a micro-needle into the slice.

Decellularizing of Organotypic Slice

Sometimes, xenogeneic and allogeneic cellular antigens can induce an inflammatory response or an immune-mediated rejection of the tissue; however, components of the extracellular matrix (ECM) are generally conserved among species and are tolerated well even by xenogeneic recipients. ECM-derived biological scaffolds can be used for creating a three-dimensional microenvironment for stem cell growth. One of the challenges of generating biological scaffolds is to efficiently remove all cellular and nuclear material while minimizing any adverse effect on the composition, biological activity, and mechanical integrity of the remaining ECM.

In some embodiments, the organotypic slice of the present invention is decellularized. In some embodiments, the method of the present invention further comprises decellularizing the organotypic slice. In some embodiments, decellularizing the organotypic slice generates a scaffold free of cellular components. In some embodiments, the organotypic slice of the present invention comprises a modified component (e.g., an extracellular matrix component, a cellular component, a genetic component). In some embodiments, the method of the present invention further comprises modifying a component (e.g., an extracellular matrix component, a cellular component, a genetic component) of the organotypic slice.

The organotypic slice can be decellularized (or a component of the organotypic slice can be modified) using a variety of methods (e.g., physical methods, chemical methods, biological methods). The physical treatments of organotypic slices can include but are not limited to agitation, sonication, mechanical massage, pressure, radiation, change in oxygen pressure, change in carbon dioxide pressure, change in temperature, freezing and thawing, laser capture microdissection, laser ablation, the like, or a combination thereof. These physical methods can help to disrupt the cell membrane, release cell contents, and facilitate subsequent rinsing and removal of the cell contents from the ECM.

The chemical methods include but are not limited to solubilizing cytoplasmic and nuclear cellular components using detergents, surfactants, chemotherapeutic chemicals, drugs, ionic solutions, hypertonic solutions, hypotonic solutions, and/or the like. Detergents and ionic solutions can include alkaline, acid, non-ionic detergents (Triton X-100), ionic detergents (Sodium dodecyl sulfate, SDS), sodium deoxycholate, Triton X-200, zwitterionic detergent (e.g., CHAPS), sulfobetaine-10 and -16 (SB-10, SB-16), Tri(n-butyl)phosphate, hypotonic and hypertonic solutions for cell lysis via osmotic shock, EDTA/EGTA chelating agents that bind divalent metallic ions so as to disrupt cell adhesion to ECM. For example, an organotypic slice prepared from a heart valve can be completely decellularized with 1% sodium deoxycholate (SD), 1% sodium dodecylsulfate (SDS), or 0.05% trypsin/ 0.02% EDTA (Tudorache et al., 2007, J. Heart Valve Dis. 16: 567-73).

The biological (e.g., enzymatic) methods include but are not limited to treatment with trypsin, protein or DNA endonucleases, protein or DNA exonucleases, a cytokine, a chemokine, a trophic factor, a bacteria, a virus, a protozoa, the like, or a combination thereof. A combination of physical, chemical, and enzymatic treatments may be employed.

It may be necessary to verify that the cellular portion of the organotypic slice has been removed. A variety of methods may be used to verify that the organotypic slices have been decellularized. Histological staining using Hematoxylin and Eosin can serve as a first line of inspection to determine if nuclear structures can be observed. Histological staining using Masson's Trichome, Movat's Pentachrome, or Safrin O can also be used to examine tissues for the presence of various cytoplasmic and extracellular molecules.

Immunohistochemical methods may be utilized for visualizing specific intracellular proteins, such as actin and vimentin. DAPI or Hoechst can be used for staining. DAPI and Hoechst are both fluorescent molecules that bind to the AT clusters in the minor groove of DNA for inspection for the presence of DNA. Staining with propidium iodide and PicoGreen can be used for staining, which can provide quantitative data regarding the presence of DNA within an organotypic slice. Polymerase chain reaction (PCR) assays may also be used.

Specific cells may also need to be removed from the organotypic slice. Many protocol presently exist for selective decellularization of organotypic slices (Boscia et al, 2008; Pringle et al, 2003; Pringle et al, 1997; Ding et al, 2008; Higuchi et al, 2008).

In some embodiments, the organotypic slice comprising a modified extracellular matrix component includes an organotypic slice wherein an extracellular matrix group has been reduced, decreased, depleted, ablated, increased, or mutated. In some embodiments, the extracellular matrix group comprises a structural protein, an attachment protein, a proteoglycan, a polysaccharide, a cellular adhesion molecule, an interstitial matrix component, a basement membrane component, a derivative thereof or a combination thereof. In some embodiments, the structural protein comprises a collagen, an elastin, a derivative thereof, or a combination thereof. In some embodiments, the collagen comprises a collagen I, a collagen II, a collagen III, a collagen IV, a collagen V, a collagen VI, a collagen IX, a derivative thereof or a combination thereof. In some embodiments, the attachment protein comprises a fibronectin, a laminin, a cadherin, a vitronectin, a fibrinogen, a von Willebrand factor, a thrombospondin, an osteospondin, a derivative thereof, or a combination thereof. In some embodiments, the proteoglycan comprises a heparan sulfate proteoglycan, a perlecan proteoglycan, an agrin proteoglycan, a collagen XVIII proteoglycan, a chondroitin proteoglycan, a chondroitin sulfate, a keratan sulfate proteoglycan, a protein core attached to a long chain of glyocsaminoglycans, a derivative thereof or a combination thereof. In some embodiments, the polysaccharide comprises a hyaluronic acid or a derivative thereof. In some embodiments, the cellular adhesion molecule comprises an integrin or a derivative thereof. In some embodiments, the basement membrane component comprises a collagen IV, a perlecan, a heparan sulfate proteoglycan, a laminin, an integrin, an enactin, a dystroglycan, a collagen VII, a fibrillin, a derivative thereof or a combination thereof.

In some embodiments, the organotypic slice comprising a modified cellular component includes an organotypic slice wherein a cell group has been reduced, decreased, depleted, ablated, or increased. In some embodiments, the cell group comprises a stem cell, a glial cell, an astrocyte, an oligodendrocyte, a microglia cell, a macroglia cell, a stromal cell, a neuron, an ependymal cell, a radial glia cell, a spindle neuron, a Schwann cell, a satellite cell, a hepatocyte, a leukocyte, an erythrocyte, a cardiomyocyte, a myocyte, a myotube, an oocyte, an osteoblast, an osteoclast, a T-cell, a B-cell, a fibroblast, a white adipocyte, a brown adipocyte, an epithelial cell, or a combination thereof. In some embodiments, the stem cell comprises a neural stem cell, a mesenchymal stem cell, a cancer stem cell, an adult stem cell, an embryonic stem cell, a cord blood stem cell, a stromal stem cell, an adipose-derived stem cell, a hematopoietic stem cell, a mammary stem cell, an olfactory stem cell, or a combination thereof.

In some embodiments, the organotypic slice comprising a modified cellular component includes an organotypic slice wherein a cell organelle has been reduced, decreased, depleted, ablated, increased, or mutated. In some embodiments, the cell organelle comprises a mitochondria, a vacuole, an endoplasmic reticulum, a cytoskeleton component, a Golgi apparatus component, a ribosome, a nucleus, a peroxisome, a chloroplast, a flagellum, a vesicle, or a combination thereof.

In some embodiments, the organotypic slice comprising a modified genetic component includes an organotypic slice wherein a genetic unit has been reduced, decreased, depleted, ablated, increased, or mutated. In some embodiments, the genetic unit comprises a gene, a DNA, a messenger RNA (mRNA), a ribosomal RNA (rRNA), a small temporal RNA (stRNA), a small nucleolar RNA (snoRNA), a transfer RNA (tRNA), a protein, or a combination thereof. In some embodiments, the gene is selected from one or more of the groups of central nervous system genes (e.g., chemokine C-X-C motif receptor 4 (CXCR4), glial fibrillary acidic protein (GFAP), brain derived neurotrophic factor (BDNF)); metabolic genes (e.g., glucose-6-phosphatase (G6Pase), acetyl coenzyme A carboxylase (ACC), peroxisome proliferator activated receptor gamma coactivator 1α (PGC-1α)); immunology genes (e.g., cluster of differentiation 8 (CD8), leukocyte-specific protein tyrosine kinase (LCK), variable lymphocyte receptor (VLR)); cell proliferation genes or cell cycle genes (e.g., protein 53 (p53), cyclin-dependent kinase (CDK), pericentrin); cell signaling genes (e.g., mitogen-activated protein kinase (MAPK), epidermal growth factor receptor (EGFR), protein kinase B (PKB)); mitochondrial genes (e.g., cytochrome c, coenzyme Q, carnitine acetyl transferase (CAT)); or a combination thereof. In some embodiments, the gene is selected from one or more of the groups of cytoskeletal genes (e.g., actin-binding LIM protein 1, WASP family 1, dystrobrevin beta); transporter genes (e.g., ATP-binding cassette subunit 13, solute carrier family 4, solute carrier family 1); secreted protein genes (e.g., stromal cell-derived factor 1, guanylate cyclase activator 2a, adiponectin C1Q, carboxypeptidase N polypeptide 2); ion channel genes (e.g., aquaporin 7, chloride channel 4-2, chloride channel calcium activated 3); G protein coupled receptor (GPCR) genes (e.g., purinergic receptor P2Y, G protein coupled receptor 143, hypocretin receptor 1); signaling genes (e.g., caspase 8 associated protein, regulator of G-protein signaling 20, transforming growth factor beta); protease genes (e.g., matrix metallopeptidase 8, methionine aminopeptidase 2, leucine aminopeptidase 3); phosphatase genes (e.g., myotubularin related protein 3, protein tyrosine phosphatase 4a2); membrane protein genes (e.g., CXC receptor 4, aquaporin 11, anterior pharynx defective 1a, SPFH domain family member 1); kinase genes (e.g., cyclin dependent kinase-like 3, cyclin dependent kinase 2, death-associated kinase 2); enzyme genes (e.g., adenylate cyclase 3, cytidine 5'-triphosphate, 2-4-dienoyl-coenzyme A, acetyl coenzyme A carboxylase alpha); transcription factor genes (e.g., PR domain containing 16, mortality factor 4 like 1, retinoic acid receptor gamma); nuclear hormone receptor genes (e.g., estrogen related receptor alpha, peroxisome proliferator activated receptor gamma); or non-protein encoding genes (e.g., 28S rRNA, tRNA).

In some embodiments, the organotypic slice comprises a combination of modified components, the modified components comprising a modified genetic component, a modified cellular component, a modified extracellular matrix component, or a combination thereof. Without wishing to limit the present invention to any theory or mechanism, in some embodiment, this may be advantageous, because creating a genetically engineered organism for preparing an organotypic slice may be very expensive, difficult, and time consuming to produce, particularly if more than one gene is modified in the organism. Furthermore, for example, it may be extremely expensive, difficult, and time consuming to produce a genetically engineered organism having a combination of at least one gene knocked in or overexpressed as well as at least one gene knocked out. In some embodiments, the organotypic slice comprises at least one modified component. In some embodiments, the organotypic slice comprises at least two modified components. In some embodiments, the organotypic slice comprises at least three modified components.

In some embodiments, the organotypic slice comprises at least four modified components. In some embodiments, the organotypic slice comprises at least five modified components.

Placement of Organotypic Slice on a Culture Matrix

The organotypic slices can be placed atop a membrane inside a culture dish (see FIG. 1). For example, polyacrylamide gel (e.g., 5%) cross-linked with ECM can be used with tissue culture grade glue (Roti® coll 1). A polyacrylamide gel (PAA) matrix microenvironment can provide a suitable surface for neuronal growth.

In some embodiments, a culture insert (Millicell 0.4 micrometer, Millipore) can be used with tissue culture grade glue for orientation of the organotypic slice. In some embodiments, the agarose gel can be used with tissue culture grade glue for orientation of the organotypic slice.

After preparation of the slice, it can be cultured in slice culture medium (SCM) (see Example 1 for recipe). In some embodiments, the slice is inoculated with a population of stem cells. In some embodiments, the slices having stem cells are cultured in DMEM with 10% FBS and 1% Pen/Strep. The co-culturing of stem cells in the organotypic slice promotes the viability of the organotypic slice. Co-culture of stem cells helps the organotypic slice last longer.

In some embodiments, the organotypic slices can be frozen at −80 degrees Celsius. To freeze the slices, the slices can be covered with 90% fetal bovine serum (FBS) and 10% DMSO and placed in a sealed container. The container can be set into an isopropanol freeze chamber for slow freezing down to −80 degrees Celsius.

Quality Assurance Parameters

Before the organotypic slice is used in an assay, it may be desirable to subject the slice to a variety of quality assurance (QA) parameters. In some embodiments, physical characteristics are used to determine the viability and/or quality of the organotypic slice. Physical characteristics are well know to one of ordinary skill in the art. For example, an organotypic slice of good quality should be intact and generally flat with no folds. It should not have debris attached. The organotypic slice should not have black spots.

In some embodiments, the organotypic slice can be tested for viability. For example, an index can be created with a ratio of live/dead cells in the organotypic slice. To determine the ratio, fluorescent dyes such as fluorescein diacetate (FDA) and propidium iodide (PI) may be used (Choe et al. 2004, Neuro-Chem Int. 45: 111-127). Or, a viability/cytotoxicity kit may be used (Invitrogen). Or, the slice may be stained with crystal violet (Ito, 1984).

The slice may also be subjected to a CyQUANT cell proliferation assay, a lactate dehydrogenase (LDH) assay, a CytoTox 96® Non-Radioactive Cytotoxicity Assay (Promega), viable cell counts using trypan blue staining, acridine orange staining for apoptotic cells, Fluoro-Jade staining (Fluoro-Jade is a specific and selective marker to identify neurons undergoing degeneration) (Schmued et al, 1997, Brain Res. 751: 37-46), a MTT assay for assessing metabolic activity of cells, or an electrophysiology assay such as a patch clamp and calcium influx assay.

Seeding of Stem Cells

The organotypic slices can be directly inoculated with cells (e.g., stem cells). In some embodiments, the cells can be seeded in the sides of the organotypic slice.

In some embodiments, the population of stem cells comprises a totipotent stem cell, a pluripotent stem cell, a multipotent stem cell, a unipotent stem cell, an adult stem cell, an embryonic stem cell, a cord blood stem cell, a mesenchymal stem cell, a neural stem cell, a stromal stem cell, an adipose-derived adult stem cell, a hematopoietic stem cell, a mammary stem cell, an olfactory stem cell, or a combination thereof.

In some embodiments, the population of cells (e.g., stem cells) is isolated from a mammal, for example, a human, a mouse, a rat, a rabbit, a dog, a primate, a guinea pig, a cat, a hamster, a pig, a chicken, a goat, a horse, or a cow. In some embodiments, the population of stem cells is derived from an organism, for example, a human, a mouse, a rat, a rabbit, a dog, a primate, a guinea pig, a cat, a hamster, a pig, a chicken, a goat, a horse, or a cow.

To seed the organotypic slice with a population of cells, the cells must first be collected. For example, a population of stem cells can be harvested, centrifuged for about 1 minute at 200 g, and washed with about 5 ml of neural induction medium. The cells can then be re-suspended in about 40-60 ml of neural induction medium supplemented with 20 ng/ml bovine fetal growth factor (bFGF) and transferred to a new flask. Cells in the neural induction medium can be fed every other day.

After about 2 days, aggregates of cells should form. The aggregates are ready for seeding in an organotypic slice. When the aggregates are plated on the organotypic slice, they will attach to the slice, probably over a 12 to 16 hour period. When the aggregates are plated on the slice, it is important to provide enough space for colonies to grow out without contacting each other.

The attached aggregates will collapse to form a monolayer colony after about 1 to 2 days. The cells should continue to be fed with neural induction medium with 20 ng/ml bFGF every other day.

Applications of Organotypic Slices of the Present Invention

The organotypic slices of the present invention have clinical relevance. The organotypic slices of the present invention may be used for a variety of applications. For example, the organotypic slices can be used for the differentiation of dopaminergic neurons from human embryonic stem cells (hESCs). To achieve this, the population of stem cells (e.g., hESCs) seeded in the organotypic slice can be fed with neuronal differentiation medium containing FGF8 (50 ng/ml), SHH (100 ng/ml), B27, ascorbic acid (200 µM), cAMP (1 µM), laminin (1 µg/ml), TGFβ (1 ng/ml), and trophic factors such as BDNF (20 ng/ml) and/or GDNF (50 ng/ml).

The organotypic slices can be used to characterize a population of cells (e.g., stem cells, primary brain tumor cells). To characterize the cell population seeded in the organotypic slice, the cultures may be subjected to a variety of assays and/or procedures. Assays may include but are not limited to real time PCR assays. MMP enzymatic assays, immunohistochemistry assays, immunocytochemistry assays, invasion assays, electron microscopy, and the like.

The organotypic slices can be used to monitor stem cell behaviors in real-time. For example, the organotypic slices can be embedded with real-time reporters. Real time reporters have been previously described (Sakaue-Sawano et al., 2008, Cell 132: 487-498). Behaviors such as cell cycle and migration can be observed in these slices. These real time assays can be used for testing, for example, the effects of a particular compound or agent upon a particular biological system.

In some embodiments, the organotypic slices of the present invention may be used as ex vivo models for gene therapy. In some embodiments, the organotypic slices may be used to monitor repair capabilities of stem cells.

EXAMPLE 1

Recipes

The following are examples of recipes for solutions for preparing organotypic slices according to the present invention. The solutions are not limited to these formulas and recipes.

| Complete Hank's Balanced Salt Solution (HBSS) 1× |
|---|
| 2.5 mM Hepes (pH 7.4) |
| 30 mM D-glucose |
| 1 mM CaCl$_2$ |
| 1 mM MgSO$_4$ |
| 4 mM NaHCO$_3$ |

*Add double distilled water (ddH20) to a total volume of 500 ml. Filter with a 0.2 μm filter. Store at 4° C.

Low-Melting Point (LMP) Agarose

| Low-Melting Point (LMP) Agarose |
|---|
| 0.75 g LMP agarose |
| 25 ml Complete HBSS |

*Dilute LMP agarose in HBSS in a 50 ml sterile conical tube and mix well.
*Microwave solution about 2 min on medium power.
*When agarose is dissolved, place solution in a 37° C. water bath until ready for use.
*Solution can be stored at 4° C.

Slice Culture Medium (SCM)

| Slice Culture Medium (SCM) |
|---|
| 50% Minimal essential medium (MEM) |
| 25 mM HEPES |
| 25% HBSS |
| 6.4 mg/ml glucose |
| 0.5 mM glutamine |
| 0.5 ml of 100 u/ml penicillin + 0.1 mg/ml streptomycin |

*Filter with a 0.2 μm filter.
*Add heat-inactivated horse serum to a final concentration of 25%.

Embryonic Stem Cell (ESC) Medium

| ESC Medium |
|---|
| 392.5 ml DMEM/F12 |
| 100 ml KnockOut serum replacement |
| 5 ml MEM non-essential amino acids solution |
| 3.5 μl 2-mercaptoethanol (14.3M) |
| 2.5 ml L-glutamine (200 mM) |

*Filter with a 2a 0.2 μm filter. Add 4 ng/ml bFGF just prior to feeding cells. Can be stored at 4° C. for up to 2 weeks.

Neural Induction Medium

| Neural Induction Medium |
|---|
| 490 ml DMEM/F12 |
| 5 ml N2 |
| 5 ml MEM non-essential amino acids solution |
| 500 μl heparin (2 mg/ml) |

Neural Differentiation Medium

| Neural Differentiation Medium |
|---|
| 490 ml Neurobasal medium |
| 5 ml N2 |
| 5 ml MEM non-essential amino acids solution |

For motor neuron differentiation, other components may be added to the neural differentiation medium. For example BDNF, GDNF, IGF-1, FGF8, SHH, laminin, TGF-beta, heparin, cAMP, ascorbic acid, the like, or a combination thereof.

Dispase Solution

| Dispase Solution |
|---|
| 10 mg dispase |
| 10 ml DMEM/F12 |

*Leave in a 37° C. water bath for 15 min. Filter sterilize with a 50 ml Steri-Flip before use.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An organotypic slice comprising a brain slice obtained from a brain wherein mature synapses have not been established, wherein the organotypic slice is seeded with a population of stem cells and is further disposed over a polyacrylamide gel (PAA) crosslinked with extracellular matrix (ECM) attached to a culture dish via tissue culture grade glue; wherein the organotypic slice has enhanced viability as compared to an organotypic slice comprising a similar brain slice not seeded with a population of stem cells and is disposed over PAA crosslinked with ECM attached to a culture dish via tissue culture grade glue.

2. The organotypic slice of claim 1, wherein the brain is obtained from a rodent of an age between three to nine days.

3. The organotypic slice of claim 1, wherein the enhanced viability allows the organotypic slice to live for more than about 6 months.

4. The organotypic slice of claim 1, wherein the enhanced viability allows the organotypic slice to live for more than about 12 months.

5. A method of preparing an organotypic slice from a central nervous system tissue, said method comprising:
   (a) obtaining a brain from a rodent, wherein mature synapses have not been established in the brain;
   (b) preparing a brain slice from the brain; and
   (c) disposing the brain slice over a polyacrylamide gel (PAA) crosslinked with extracellular matrix (ECM) attached via tissue culture grade glue to a culture dish.

6. The method of claim 5, wherein the brain is obtained from a rodent of an age between three to nine days.

7. The method of claim 5, wherein the method further comprises seeding the brain slice with a population of stem cells.

8. The method of claim 5, wherein the step of obtaining a brain from a rodent comprises:

(a) euthanizing the rodent and removing the brain;

(b) placing the brain in a dish of ice-cold Hank's Balanced Salt Solution (HBSS) on ice; and (c) embedding the brain in a dish of 38° C. low melting point agarose (LMP) and allowing the LMP agarose to harden.

9. The method of claim 5, wherein the step of preparing the brain slice comprises:

(a) placing the LMP agarose-embedded brain in a vibratome; and (b) slicing sections of the brain between about 250 to 300 μM in thickness.

10. The method of claim 5, wherein method further comprises microdissecting the brain slice.

* * * * *